United States Patent [19]

Giurtino

[11] Patent Number: 4,705,042

[45] Date of Patent: Nov. 10, 1987

[54] PACING SYSTEM ANALYZER HAVING PROVISION FOR DIRECT CONNECTION OF PACER TO PACING LEADS

[75] Inventor: Joel F. Giurtino, Miami, Fla.

[73] Assignee: Cordis Corporation, Miami, Fla.

[21] Appl. No.: 736,635

[22] Filed: May 21, 1985

[51] Int. Cl.$^4$ .............................................. A61N 1/36
[52] U.S. Cl. .............................................. 128/419 PT
[58] Field of Search .......................... 128/419 PT, 697

[56] References Cited

U.S. PATENT DOCUMENTS

| 3,757,790 | 9/1973 | Herrmann | 128/419 PT |
| 3,768,487 | 10/1973 | Rose | 128/419 PT |
| 4,423,732 | 1/1984 | Tarjan et al. | 128/419 P |

Primary Examiner—William E. Kamm
Attorney, Agent, or Firm—Lockwood, Alex, FitzGibbon & Cummings

[57] ABSTRACT

A pacing system analyzer for analyzing and verifying the performance of a pacer system which includes an implanted pacer lead and a pacer to be implanted. A patient cable includes a first plug member for connecting the implanted cardiac lead to a first connector on the analyzer. The pacer includes a second plug member for connecting the pacer to a second connector on the analyzer. The first and second plug connections are of opposite gender and complementary to enable the pacer to be connected directly to the patient cable in an alternative, operating mode of the analyzer.

2 Claims, 9 Drawing Figures

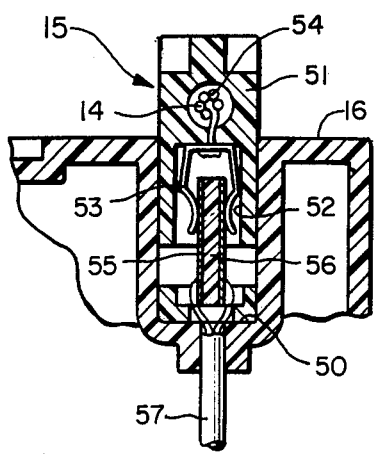
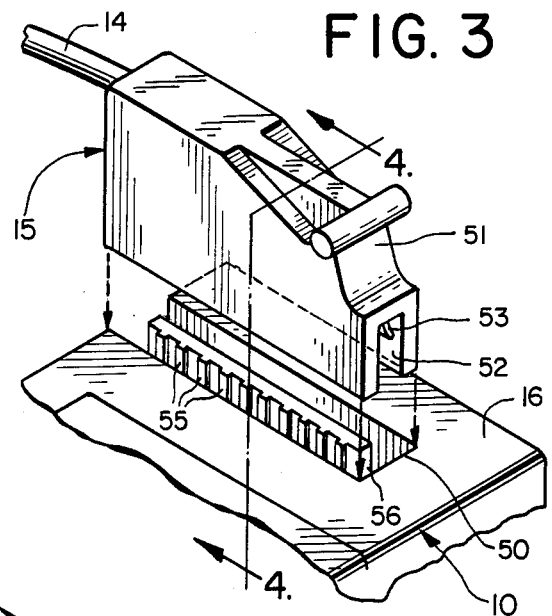
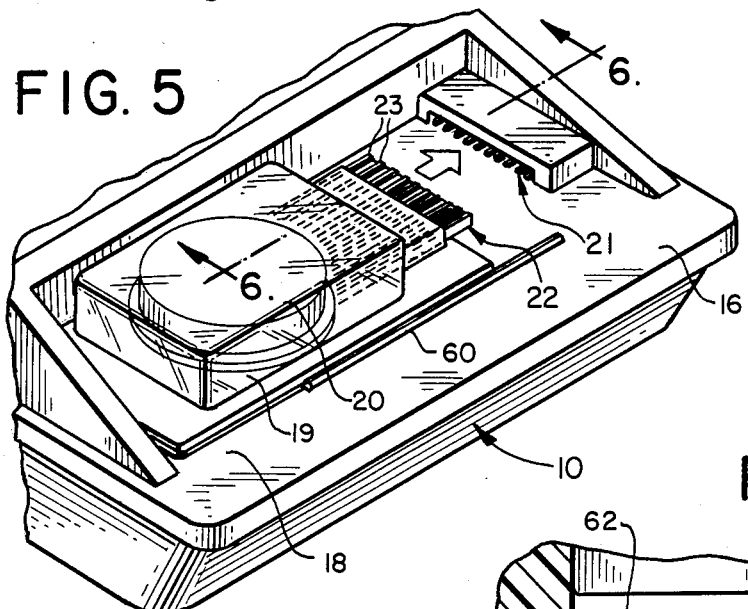
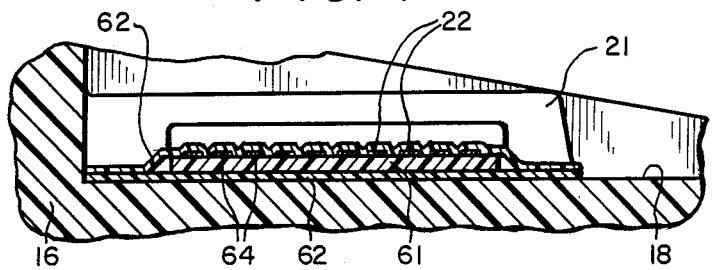
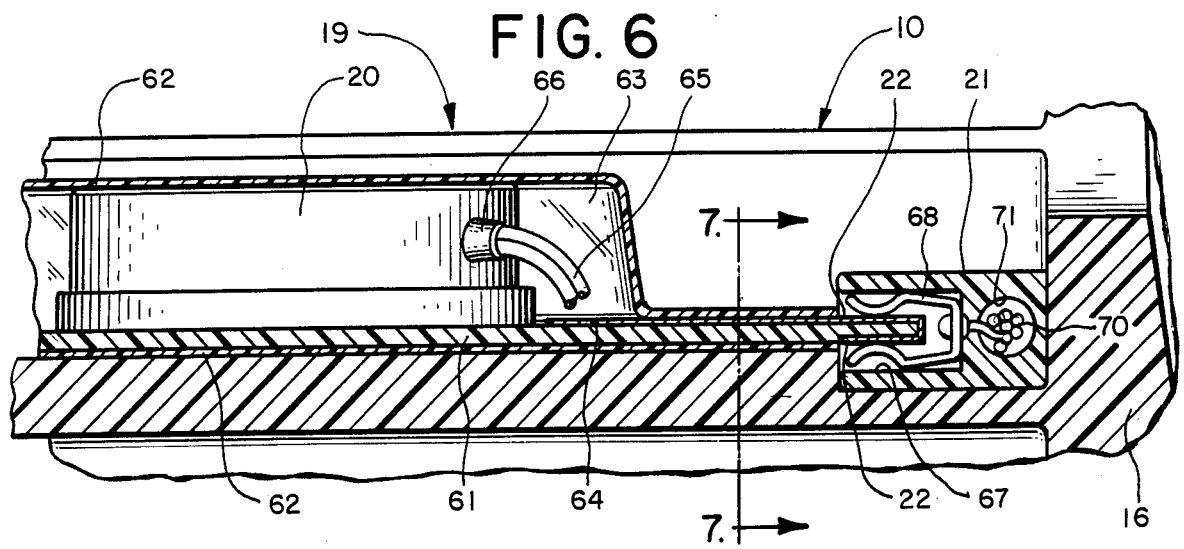

PACING SYSTEM ANALYZER HAVING PROVISION FOR DIRECT CONNECTION OF PACER TO PACING LEADS

BACKGROUND OF THE INVENTION

The present invention relates generally to a method and apparatus for analyzing and verifying the operation of a cardiac pacer prior to implantation, and more particularly to a system for verifying pacer operation which prior to implantation is interposed between the pacer and implanted pacer leads, and which can be readily removed to establish a direct connection between the pacer and the pacer leads when required.

To assist physicians in treating cardiac disorders of the type for which the use of implantable cardiac pacers is indicated, pacer system analyzers (PSA's) have been developed. These devices are used immediately prior to the time of pacer implantation to efficiently measure the parameters of the pacer system, which includes the patient's heart, the pacer to be implanted, and the previously implanted pacer leads, without the need to perform separate procedures requiring multiple interconnections and an undesirably long time to complete. Pacer System Analyzers test the pacer to be implanted for proper programming and operation, not only while connected in a simulated pacing system environment, but also while operating in the actual system in which they are to be used. Moreover, pacer system analyzers are preferably equipped to generate pacing pulses as required to support the patient during the pacer implantation process, independently of the pacer to be implanted.

By using a pacer system analyzer, a physician is able to adjust the operating parameters of a pacer and the implanted pacer leads to suit the specific needs of an individual patient before the pacer has been fully implanted and the implantation surgery completed. This minimizes the need for inconvenient and potentially injurious post-implantation adjustment of the pacer or the pacer leads.

Typically, when utilized to measure and analyze cardiac system parameters, pacer system analyzers have been connected between the implanted cardiac leads and the pacer terminals. Separate sets of connecting terminals have been provided, and individual sets of leads have been required between the exposed ends of the cardiac leads and the analyzer, and between the pacer terminals and the analyzer.

In the event it was necessary to remove the analyzer from the system, as when required in treating another patient, or in the event of a malfunction in the analyzer, there was no efficient way in prior pacer system analyzers of connecting the pacer to the cardiac leads so that the pacer could pace the heart directly. Instead, it was necessary for the operator to first disconnect the connecting leads from the pacer and from the cardiac leads, so that the exposed ends of the pacer leads could be connected directly to the pacer.

The present invention provides a pacer system analyzer which includes a patient lead connector and a pacer connnector which are electrically and mechanically compatible, and connecting cables for establishing electrical connection between these connectors and the pacer leads and the pacer, whereby the connecting cables can be readily disconnected from the analyzer and connected to each other to provide direct pacing by the pacer. This obviates the need for adding or removing cables from the system, or for making direct interconnections between the components. Consequently, a rapid changeover between pacing sources is possible to minimize trauma to the heart.

Accordingly, it is a general object of the present invention to provide a new and improved pacer system analyzer.

It is a more specific object of the present invention to provide a pacer system analyzer which can be readily removed from the pacing system with minimal interruption of a patient's pacing regimen.

SUMMARY OF THE INVENTION

The invention is directed to a pacer system analyzer for verifying and analyzing the operation of a cardiac pacing system comprising a patient heart, implanted patient pacer leads, and a pacer to be implanted. The analyzer includes a first connector for establishing electrical communication with the pacing leads, and a second connector for establishing electrical communication with the pacer. A first cable assembly is connected between the pacer leads and the first connector. A second cable assembly is connected between the pacer and the second converter. The first and second connectors and the first and second cable assemblies connecting therewith are electrically and mechanically compatible and of opposite gender, whereby the cable assemblies upon removal from the analyzer are directly connectable to establish electrical communication between the cardiac lead and the pacer.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 3 is an enlarged perspective view of the patient lead connector of the pacer system analyzer.

FIG. 4 is a cross-sectional view of the patient lead connector taken along line 4—4 of FIG. 3.

FIG. 5 is an enlarged perspective view of the pacer connector provided in the pacer system analyzer showing an implantable cardiac pacer positioned for insertion in the connector.

FIG. 6 is a cross-sectional view of the connector taken along line 6—6 of FIG. 5.

FIG. 7 is a cross-sectional view of the pacer connector taken along line 7—7 of FIG. 6.

DESCRIPTION OF THE PREFERRED EMBODIMENT

Figure 1:
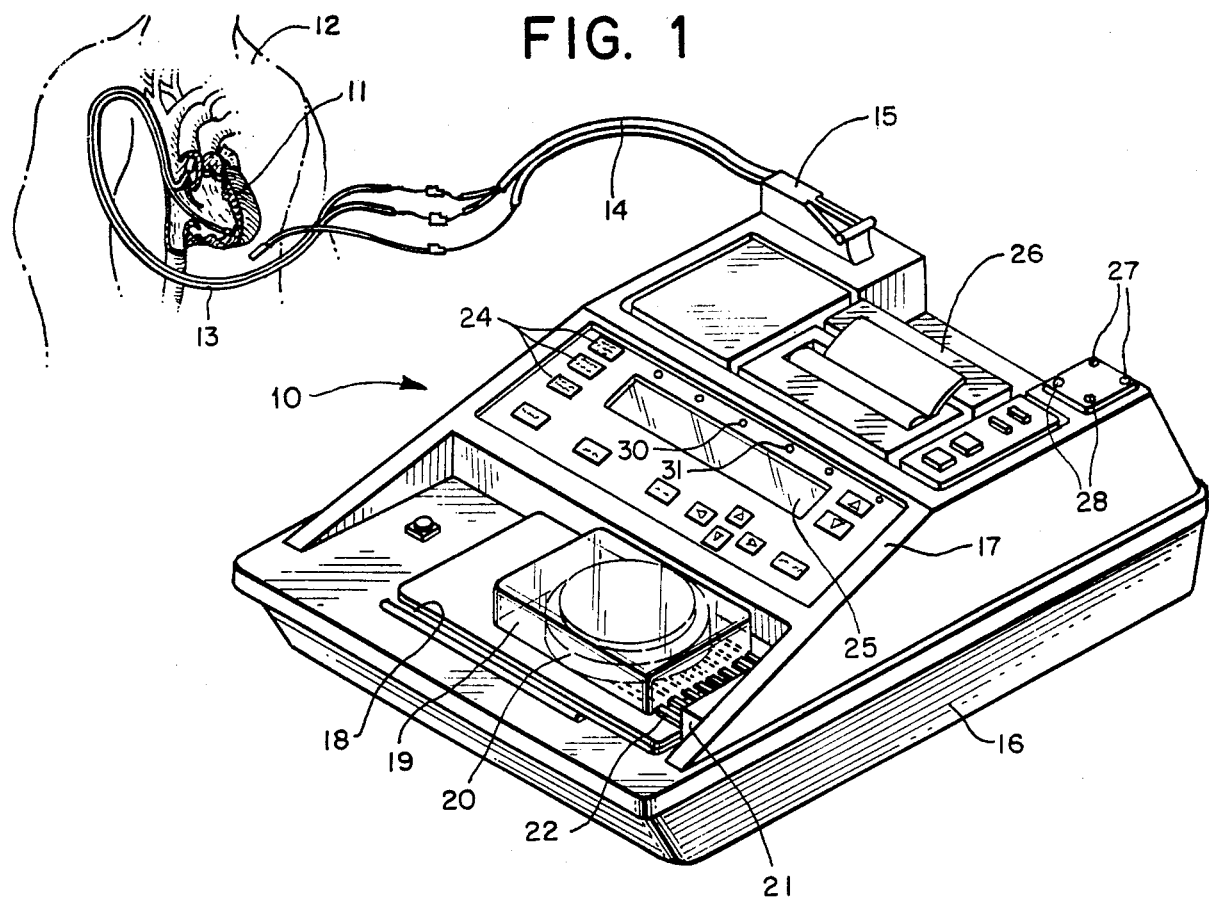
FIG. 1 is a perspective view of a pacer system analyzer incorporating an alternative direct connection between pacer and patient lead construction in accordance with the invention.

Referring to the figures, and particularly to FIG. 1, a pacer system analyzer (PSA) 10 is shown which incorporates a patient lead and pacer interconnection system constructed in accordance with the invention. As illustrated, the pacer system analyzer is connected to the heart 11 of a patient 12 by means of an implantable cardiac lead 13, which may be conventional in construction and operation. The cardiac lead is electrically connected to the analyzer 10 by means of a patient connecting lead 14 and a multicontact connector assembly 15.

The pacer system analyzer 10 is contained within a generally rectangular housing 16 formed of a durable insulating plastic or like material and includes a sloping, generally flat control panel 17. A portion of the housing is formed to provide a receptacle 18 for receiving a sealed package 19 containing a sterile implantable cardiac pacer 20. A pacer receptacle 21 in recess 18 engages a pacer connector assembly 22 comprising a plurality of electrical contacts 23 formed on package 19 to provide electrical communication between the analyzer and pacer 20.

Panel 17 includes a plurality of pressure sensitive user-actuable push button controls 24 and a liquid crystal display (LCD) 25. The analyzer operates in one of several user-selected modes in accordance with entered key stroke commands. To assist the user in selecting the appropriate operating mode, a series of internally generated instructions and a plurality of measured pacer system operating parameters are displayed on LCD 25. A plotter mechanism 26 provides a display of sensed EKG signals, as well as a printed record of measured pacer system operating parmeters and measured patient parameters. Two sets of IECG electrodes 27 and 28 provide isolated atrial and ventricular cardiac signals for connection to external instrumentation. Atrial and ventricular pacing lights 30 and 31, located along the top edge of control panel 17, provide an indication of pacer operation.

The patient's heart 11, implanted cardiac lead 13, and pacer 20 together form a pacer system. Analyzer 10 functions to measure various parameters of this system and to thereby assist a physician in selecting, implanting and adjusting the pacer leads and pacer for maximum effectiveness. Additionally, proper operation of the system can be verified before final implantation, and pacing pulses for supporting the patient during pacer system implantation can be generated.

Figure 2:
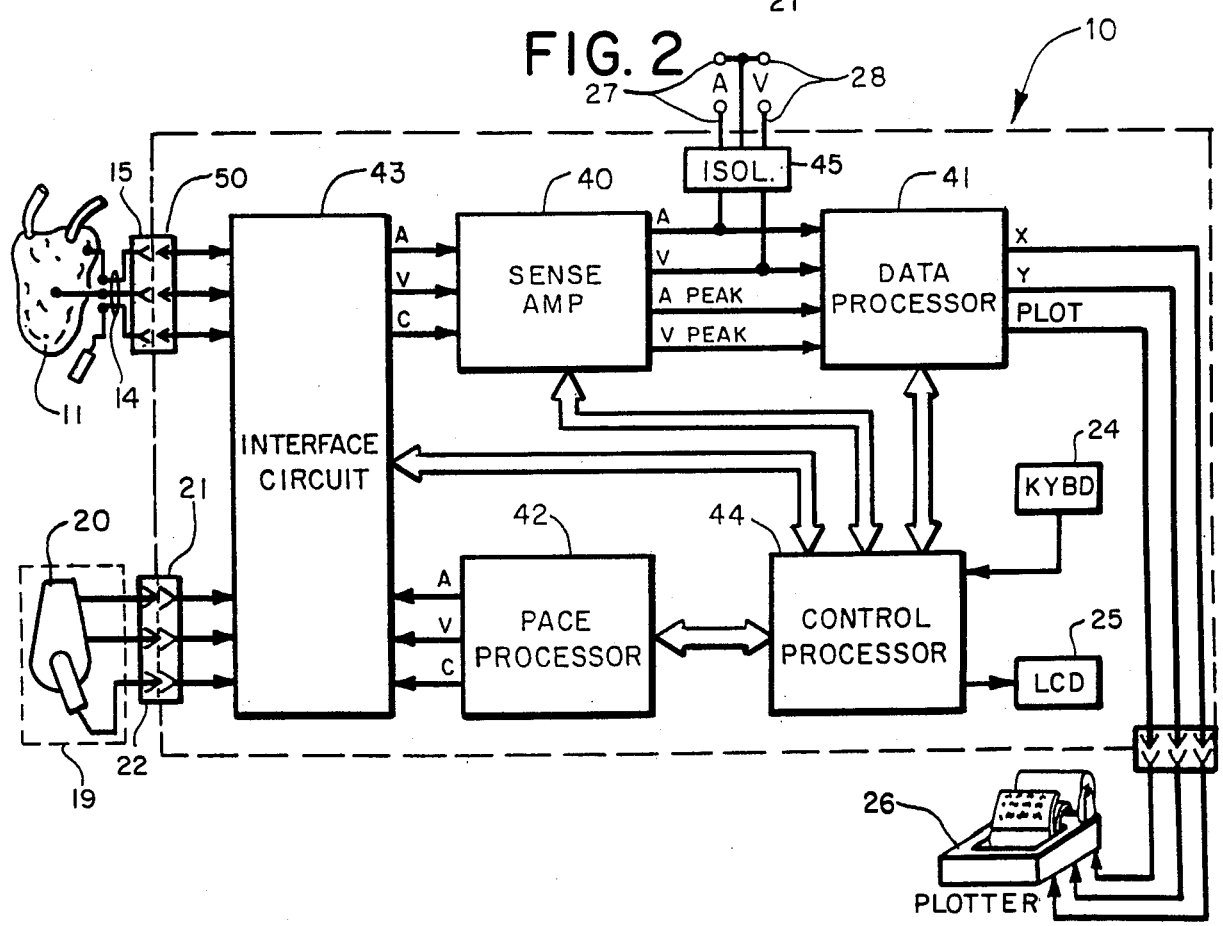
FIG. 2 is a simplified functional block diagram showing the principal components of the pacer system analyzer of FIG. 1.

Referring to the simplified pacer system analyzer functional block diagram of FIG. 2, analyzer 10 includes a sense amplifier 40 for amplifying sensed cardiac signals, a data processor 41 for processing the sensed signals, a pace processor 42 for genrating atrial and/or ventricular pacing signals, an interface circuit 43 for coupling the patient's heart 11 and implantable pacer 20 to the pacer system analyzer, and a control processor 44 for controlling the operation of the analyzer components.

Control processor 44 is preferably microprocessor based and is programmed to generate system control voltages in response to user-entered keystroke commands from control panel 17 (FIG. 1). Additionally, the control processor may generate a series of user instructions for display on LCD 25.

With the pacer system analyzer 10 interposed between the pacer leads and the pacer as shown in FIG. 1, pace processor 42 generates pacing pulses for application to heart 11 to facilitate measurement of patient parameters and to provide basic patient life support. Atrial and ventricular pacing pulses of predetermined amplitude, duration and rate are generated in accordance with applied pace control signals from control processor 44. The pacing pulses are transferred from the pace processor through interface circuit 43 for application to the heart 11 through cardiac lead 13 and patient lead 14.

As further illustrated in FIG. 2, pacer 20 is connected by pacer receptacle 21 and connector assembly 22 to interface circuit 43. Upon application of an appropriate control signal from control processor 44, interface circuit 43 couples cardiac lead 13 to pacer 20 whereupon the heart is paced by the pacer. Thus, by producing appropriate control signals, the control processor can cause the heart to be paced by either pace processor 42 or by implantable pacer 20.

Atrial and/or ventricular intracardiac signals detected by cardiac lead 13 are applied to respective inputs of sense amplifier 40. The sense amplifier generates atrial and/or ventricular strobe signals for application to control processor 44 upon the occurrence of atrial or ventricular intracardiac signals above a predetermined threshold. Additionally, the sense amplifier provides amplified atrial and ventricular signals for application to data processor 41 and for application to IECG terminals 27 and 28 through an isolation circuit 45, as well as signals indicative of the peak atrial and ventricular R-waves sensed by cardiac lead 13. Data processor 41 performs the mathematical operations required to calculate various patient or pacer system operating parameters for display on LCD 25 or for printing by printer 26.

Referring to FIG. 3, pacer system analyzer 10 is seen to include a patient receptacle 50 for receiving the patient connector assembly 15 associated with the pacer lead interconnect cable 14. As shown in FIG. 4, connector 15 includes a housing 51 having a slot-shaped recess 52 within which a plurality of electrical contacts 53 are provided in spaced side-by-side relationship. Cable 14 is received within a recess 54 within housing 51. The cable contains ten individual conductors which connect with respective ones of the ten spring contacts 53 as shown in FIG. 4. Each of the contacts 53 is generally U shaped with the ends thereof inwardly biased so as to receive a mating contact therebetween.

Within receptacle 50 the pacer system analyzer 10 includes a male contact assembly comprising ten individual strip-like contacts 55 arranged on an electrically non-conducting insulator board 56 so as to engage respective ones of female contacts 53 when connector assembly 15 is inserted into receptacle 50. The individual contacts 55 are connected to respective conductors of a cable 57 associated with circuitry within analyzer 10. In practice, contacts 55 may extend to both opposing surfaces of insulator board 56 so as to provide a positive low resistance electrical contact with spring contacts 53 when connector 15 is seated in receptacle 50, as shown in FIG. 4.

Referring to FIGS. 5–7, the pacer 20 to be implanted is seen to be contained within a semi-rigid electrically-insulating transparent housing 19 formed of plastic or similar material. The construction and function of this pacer housing is described in U.S. Pat. No. 4,423,732, which is assigned to the same assignee as the present invention. As shown in FIG. 5, the pacer 20, while hermetically sealed within housing 19, is received within receptacle 21 of analyzer 10 by insertion into the receptacle. A raised rib 60 may be provided on the top surface of housing 16 to guide the pacer package 19 into the receptacle.

Figure 9:
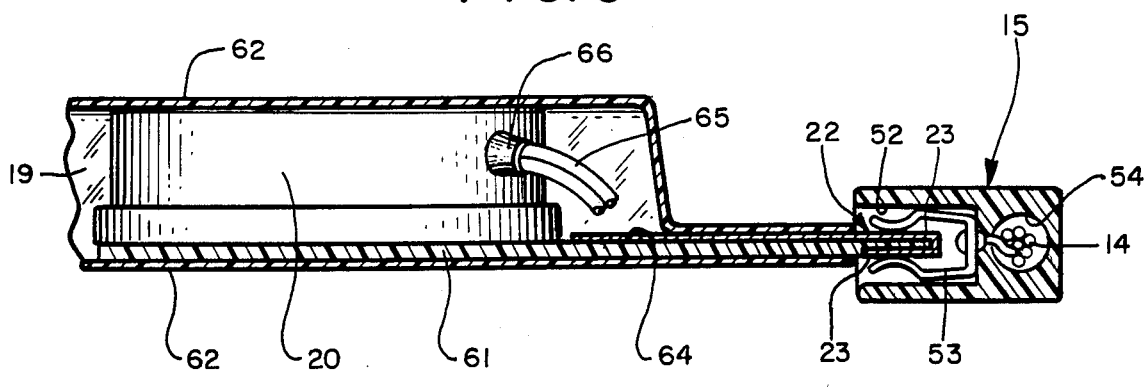
FIG. 9 is an enlarged cross-sectional view of the interconnection of the patient lead and the pacer taken along line 9—9 of FIG. 8.

Alternatively, the pacer to be implanted may be connected unpackaged within the sterile field, with a short connecting cable similar to conductors 65 having a plug for insertion into the pacer connector port 66 at one end, as shown in FIG. 9, and a connector similar to connector assembly 22 for connection with the pacer system analyzer at its other end, as shown in FIG. 6. This cable would be subsequently removed prior to implantation of the pacer, the cardiac lead 13 then being connected directly to the pacer in a conventional manner.

As best shown in FIG. 6, the pacer package basically comprises a rigid electrically non-conductive base member 61 on which the pacer 20 is mounted. A housing 62 formed of a transparent semi-rigid plastic material is attached to the surface of base member 61 by means of adhesive and is so formed as to provide an enclosed sterile compartment 63 within which the pacer 20 is contained. Extending on the upper surface (as viewed in FIG. 6) of base member 61 is a narrow strip of electrically conductive foil 64 which extends from a location within compartment 63 to a location adjacent the end of the base member. The exposed portion of foil 64 forms an electrical contact surface 23. In practice ten such contacts are provided on the top surface of carrier member 61 to form the pacer connector 22.

Depending on the type of pacer 20 provided, and hence the number of connections associated with the pacer, certain of the contacts 23 are connected by individual conductors 65 to terminals of pacer 20 at the pacer connector port 66, which may be conventional in construction. As shown in FIG. 7, in practice ten foil strips 64 may be provided extending in parallel equi-spaced relationship across the base member 61. Each of these strips may in addition extend around the edge of the base member to provide an additional contact surface 23 on the bottom of the carrier member, as shown in FIG. 6.

Within receptacle 21 there is provided a slot-shaped recess 67 for receiving the contact end of pacer housing 19. Within this recess is provided a plurality of U-shaped contacts 68 arranged side-by-side for engaging respective ones of contacts 23. Electrical connections to contacts 68 are provided by individual conductors within a cable 70 received within a recess 71 in the housing of pacer receptacle 21.

When the pacer package 19 is inserted in receptacle 21 as shown in FIG. 6, individual contacts 23 associated with pacer 20 engage individual contacts 68 to establish electrical communication between pacer 20 and the circuitry of pacer system analyzer 10. By reason of the double wiping action of the U-shaped contacts 68, positive low-resistance electrical connections are established. This is particularly important in the present application because of the criticality of maintaining pacing pulses to the heart. Since electrical connections are established without breaking the hermetic seal within which pacer 20 is packaged, the pacer remains in a sterile condition ready for implantation in the patient when the verification and analysis procedure undertaken by the pacer system analyzer 10 has been completed.

Upon completion of the procedure, or in the event of a malfunction of pacer system analyzer 10, or in the event that the analyzer 10 is suddenly needed for another procedure, there is provided, in accordance with the invention, a means by which the pacer system analyzer 10 can be bypassed and the pacer 20 can be quickly and easily connected directly to cardiac leads 13, without the necessity of disconnecting and reconnecting individual connections, and without disconnecting the cardiac leads from patient cable 14 or breaking the hermetic seal of pacer package 19. To this end, patient lead connector assembly 15 is constructed to be compatible with the pacer connector assembly 22 of pacer housing 19 such that the contacts 23 associated with pacer 20 engage respective contacts 53 of plug assembly 15.

To establish the by-pass connection, it is merely necessary to remove connector assembly 15 from patient lead receptacle 50 and remove pacer package 19 from pacer receptacle 21. The pacer connector assembly 22 of housing 19 is then inserted into recess 52 of connector assembly 15, causing the necessary connections to be established. The non-conductive base 56 of connector assembly 15 is constructed to correspond in thickness to the base 61 of pacer package 19. Furthermore, contacts 23 are positioned on base 61 so as to conform in position and spacing to contacts 55 on base 56. In practice, connection may be established by the ten contacts to unipolar (UNIP), bipolar (BIP) lead configurations in either the atrial or ventricle, or both, of the patient heart 11. By reason of the double contact area provided for each connection, the connections are mechanically secure and of low electrical resistance, thereby providing the desired reliability for pacing applications.

Figure 8:
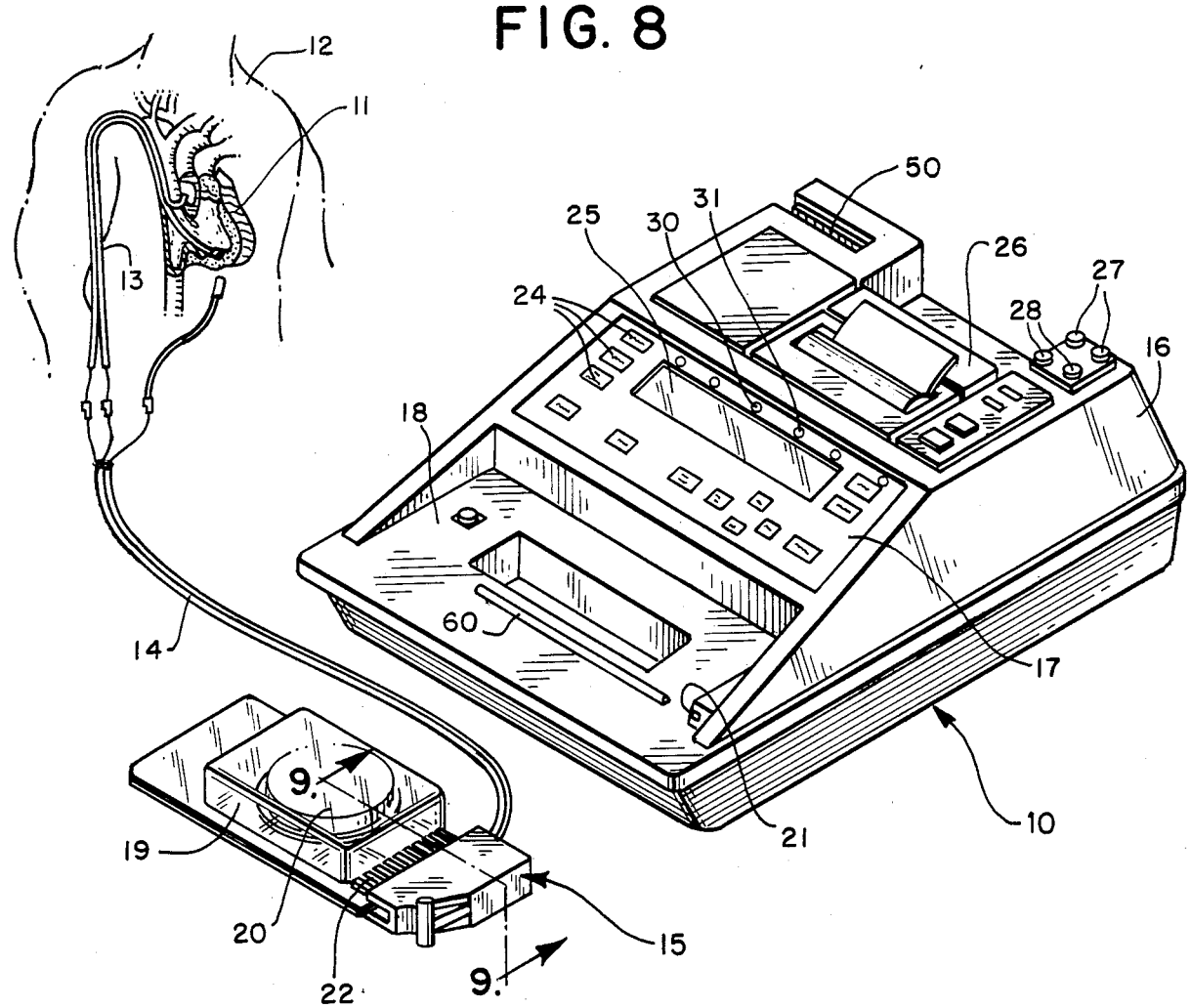
FIG. 8 is a perspective view of the pacer system analyzer system of FIG. 1 in an alternative operating mode showing the implantable pacer connected directly to the patient lead.

As a final step after the pacer has been disconnected from the pacer system analyzer 10 and reconnected directly to pacer lead 13, as shown in FIG. 8, the pacer 20 may be removed from its package 19 and implanted in the patient. At this time, the connections between the patient lead 14 and the cardiac lead, collectively identified as 72 in FIG. 8, are disconnected. At the same time, the connections to pacer 20 established by conductors 65 are broken. The pacer is then quickly reconnected, the ends of cardiac lead 13 being connected to appropriate terminals in the pacer. The pacer is then implanted in the patient.

By reason of the compatibility of connector assembly 15 and pacer connector assembly 22 of pacer package 19, the pacer system analyzer 10 can be quickly bypassed when required for other purposes, or in the event of a malfunction, or upon completion of the analysis and verification procedure. Because of the unique complementary construction of receptacles 50 and 21 of the pacer system analyzer 10, and the connector assemblies 15 and 22, the electrical connections are established with a high degree of mechanical and electrical continuity.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A pacer system analyzer for verifying the operation of a cardiac pacing system including an implanted pacer lead and a cardiac pacer to be implanted, comprising:
   a pacer system analyzer including an instrument housing;
   first multi-contact connector receptacle means in said housing of one gender for establishing electrical communication between the pacer lead and said analyzer;
   second multi-contact connector receptacle means in said housing of opposite gender from said first connector receptacle means for establishing electrical communication between the pacer and said analyzer;
   first connector means for connection between the pacer lead and said first connector receptacle means and including a first multi-contact connector plug of opposite gender to and mating with said first connector receptacle means for establishing electrical communication between the pacer lead and said analyzer;
   second connection means for connection between the pacer and said second connector receptacle means and including a second multi-contact connector plug of opposite gender to and mating with said second connector receptacle means for establishing electrical communication between the pacer and said analyzer; and
   said first and second connector plugs being electrically and mechanically compatible and of opposite gender, whereby said first and second connection means are matable only with respective ones of said first and second connector receptacle means when in communication with said analyzer, and upon removal from said analyzer are connectable with each other to establish electrical communication between the pacer lead and the cardiac pacer.

2. A pacer system analyzer as defined in claim 1 wherein one of said multi-contact connector plugs comprises a plurality of generally U-shaped contacts, and the other of said multi-contact connector plugs comprises a generally flat base member having a like plurality of strip-like contacts disposed thereon for engaging respective ones of said U-shaped contacts, said strip-like contacts extending to both sides of said base member, whereby electrical contact is established with both sides of said U-shaped contact when said connector plugs are connected.

* * * * *